US00PP14277P29

(12) United States Plant Patent

Hanes

(10) Patent No.: US PP14,277 P2
(45) Date of Patent: Nov. 4, 2003

(54) PETUNIA PLANT NAMED 'REFLEC PUR'

(50) Latin Name: *Petunia hybrida*
Varietal Denomination: Reflec Pur

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/390,954
(22) Filed: Mar. 17, 2003
(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates, PC

(57) ABSTRACT

A petunia cultivar particularly distinguished by purple colored flowers, compact habit and good basal branching.

1 Drawing Sheet

Genus and species: Petunia hybrida.
Variety denomination: 'Reflec Pur'.

BACKGROUND OF THE NEW PLANT

The present invention comprises a new and distinct cultivar of petunia, botanically known as Petunia hybrida, and hereinafter referred to by the cultivar name 'Reflec Pur'. The new cultivar is asexually reproduced from vegetative cuttings and tissue culture resulting from the cross of the seed/pod parent 'Purple Wave', a single purple commercial line that is unpatented×98-75-4, a double rose, proprietary line that is unnamed and unpatented.

'Reflec Pur' is a product of a planned breeding program intended to create new petunia plants with purple colored flowers, compact habit, good basal branching and moderately vigorous growth.

The new cultivar was created in 1999 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Reflec Pur'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light. Plant had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright and decumbent.
Growth and branching habit: Good vigorous habit, well-branched, full plant.
Height: From soil level to top of blooms: Approximately 10–20 cm.
Width: Approximately 50–60 cm including flowers.
Time to produce a finished flowering plant: 11–13 weeks.
Outdoor plant performance: Full sun; free-flowering through the summer; some heat tolerance; Used as a hanging plant, mixed containers, window boxes and mass plantings.
Time to initiate roots: Approximately 20–26 days in the greenhouse.
Root description: Fibrous, white.

THE LEAVES

Arangement: Alternate, upper leaves Sub-opposite.
Length: 4.5–4.9 cm.
Width: 3.4–3.9 cm.
Leaf blade shape: Ovate.
Leaf margin: Entire.
Apex aspect: Acute.
Base aspect: Acuminate.
Leaf color: Upper side: RHS 137A (green) Underside: RHS 138A (green).
Texture: Glandular hairs of various sizes.
Venation: Palmate.
Venation color: RHS 144B (yellow-green).
Petiole length: 0.3–0.4 cm.
Petiole diameter: 0.2 cm.
Petiole color: RHS 144B (yellow-green).
Petiole texture: Many glandular hairs of various sizes.

THE STEM

Length: 40–55 cm.
Diameter: 0.3–0.4 cm.
Internode length: 4.05–5.0 cm.
Color: RHS 144B (yellow-green).
Texture: Many glandular hairs of various sizes.
Stem anthocyanin: None.
Peduncle color: RHS 144A (yellow-green).
Peduncle length: 3.2–3.5 cm.
Peduncle diameter: 0.2 cm.
Peduncle texture: Many glandular hairs of various sizes.

THE BUD

Shape: Obovate.
Diameter: 0.7–1.0 cm.
Length: 0.9–1.1 cm.
Color at tight bud: RHS 59A (red-purple) & slight hint of RHS 149A (yellow-green).

THE FLOWER

Blooming habit: Continuous all through the growing season. Good floriferousness.
Inflorescence type: Flowers solitary in upper leaf axis.
Young flower color: Front side; RHS 71B (red-purple) but a little more intense.
Young flower floret diameter: 4.5–5.0 cm.
Mature flower color: Front side, close to but more intense than RHS 71B (red-purple) base color; hint of RHS 175A (greyed-orange) mid-vein; Underside, RHS 70A/B (red-purple) base color; RHS 165A (greyed-orange) mid-veins.
Corolla color inside: RHS N74C (red-purple) base color; RHS 79A (purple) heavy veining.
Corolla tube length: 1.7–2.0 cm to the flare.
Corolla outside texture: Many glandular hairs of various sizes.
Floret form and number of petals: Fully double, funnel form, petals have 5–8 mid-veins; petals fused at base.
Flower (limb) diameter: 6.0–6.5 cm.
Petal apex shape: Semi-pracmorse.
Petal margin: Entire.
Waviness of petals: Weak to moderate.
Petal lobation: Moderate.
Petal texture: Papillose.
Sepals: 5.
Sepal color: RHS 138B (green).
Sepal length: 1.4–1.6 cm.
Sepal width: 0.3–0.4 cm.
Sepal shape: Oblong.
Sepal apex: Obtuse.
Sepal texture: Many glandular hairs of various sizes.
Lastingness of individual blooms: 4–8 days.
Fragrance: None.

THE REPRODUCTIVE ORGANS

Stamens: 6–10, some fused to petal base.
Filament color: RHS 149D (yellow-green).
Pollen color: RHS 198B (greyed-green).
Pistil: 3 to 5.
Stigma: RHS 144B (yellow-green).
Style color: RHS 150C (yellow-green).
Fruit seed set: Not observed.

DISEASE AND INSECT RESISTANCE

Not observed.

COMPARISON WITH KNOWN CULTIVARS

Compared to its female parent 'Purple Wave' as follows: The female plant is earlier to flower, has single flowers and is more trailing in growth than the 'Reflec Pur'.

Compared to its male parent 98-75-4 as follows: The male parent has a rose colored flower on a densely growing plant, while the 'Reflec Pur' plant has purple flower on a less dense more upright plant.

I claim:

1. A new and distinct petunia plant as shown and described herein.

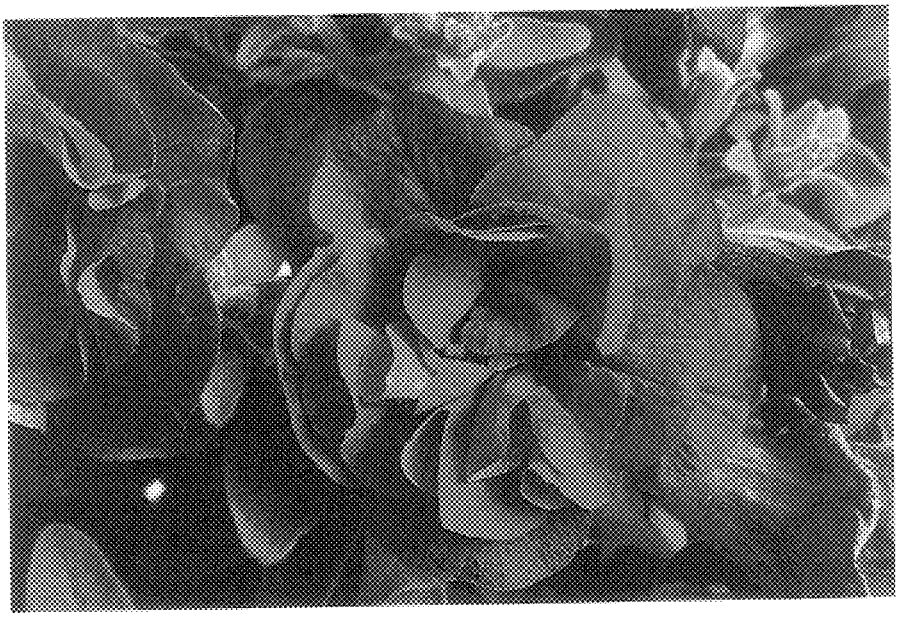

* * * * *